US011092600B2

(12) United States Patent
Colin et al.

(10) Patent No.: US 11,092,600 B2
(45) Date of Patent: Aug. 17, 2021

(54) METHOD FOR THE REAL-TIME DETECTION OF MICROORGANISMS IN A LIQUID CULTURE MEDIUM BY AGGLUTINATION

(75) Inventors: Bruno Colin, Marcy l'Etoile (FR); David Mosticone, Sainte-Consorce (FR); Jean-Claude Raymond, Bessenay (FR); Thierry Sofia, Saint-Genis-les-Ollieres (FR); Antoine Vimont, Lyons (FR)

(73) Assignee: BIOMERIEUX, Marcy l'Etoile (FR)

(*) Notice: Subject to any disclaimer, the term of this patent is extended or adjusted under 35 U.S.C. 154(b) by 501 days.

(21) Appl. No.: 12/918,159

(22) PCT Filed: Mar. 12, 2009

(86) PCT No.: PCT/FR2009/050415
§ 371 (c)(1),
(2), (4) Date: Aug. 18, 2010

(87) PCT Pub. No.: WO2009/122069
PCT Pub. Date: Oct. 8, 2009

(65) Prior Publication Data
US 2011/0020861 A1 Jan. 27, 2011

(30) Foreign Application Priority Data
Mar. 14, 2008 (FR) ........................ 0851655

(51) Int. Cl.
*G01N 33/569* (2006.01)
*C12Q 1/04* (2006.01)
*G01N 33/53* (2006.01)

(52) U.S. Cl.
CPC ............. *G01N 33/569* (2013.01); *C12Q 1/04* (2013.01); *G01N 33/5304* (2013.01)

(58) Field of Classification Search
None
See application file for complete search history.

(56) References Cited

U.S. PATENT DOCUMENTS

| | | | |
|---|---|---|---|
| 4,355,102 A * | 10/1982 | Quash | 435/5 |
| 4,659,658 A | 4/1987 | McCarthy et al. | |
| 4,661,350 A * | 4/1987 | Tsurumizu et al. | 424/242.1 |
| 5,217,715 A | 6/1993 | Krivan et al. | |
| 5,286,452 A * | 2/1994 | Hansen | G01N 33/4905 422/73 |
| 5,415,997 A * | 5/1995 | Atrache | G01N 33/569 435/174 |
| 5,418,140 A * | 5/1995 | Chang et al. | 435/7.32 |
| 5,496,706 A | 3/1996 | Kuusela et al. | |
| 2005/0118660 A1 | 6/2005 | Sciortino, Jr. | |
| 2006/0246535 A1* | 11/2006 | Burns | C12Q 1/04 435/34 |
| 2007/0218522 A1* | 9/2007 | McCoy | C12Q 1/04 435/34 |

FOREIGN PATENT DOCUMENTS

| | | |
|---|---|---|
| EP | 0 561 722 A1 | 9/1993 |
| EP | 1 199 567 A1 | 4/2002 |
| WO | WO 94/28163 A1 | 12/1994 |
| WO | WO 00/12674 A1 | 3/2000 |
| WO | WO 01/09370 A2 | 2/2001 |
| WO | WO 2005/068647 A2 | 7/2005 |

OTHER PUBLICATIONS

Sun et al., "Food-Borne Pathogens Use of bioluminescent *Salmonella* for assessing the efficiency of constructed phage-based biosorbent," Journal of Industrial Microbiology and Biotechnology, vol. 27, pp. 126-128 (2001).*
Orduna et al. (Journal of Clinical Microbiology, vol. 38, No. 11 pp. 4000-4005; 2000).*
Free dictionary definition of peptone (accessed at http://www.thefreedictionary.com/peptone on Feb. 3, 2015).*
Brucellosis diagnostic (BRUCELLACAPT®) web page (accessed https://web.archive.org/web/20050223001516/http://www.reactolab.ch/Vircell/BRUCELLOSIS.htm on Feb. 23, 2005).*
Free dictionary definition of peptone (accessed at http://www.thefreedictionary.com/peptone on Feb. 3, 2015; of record).*
Sun et al., "Food-Borne Pathogens Use of bioluminescent *Salmonella* for assessing the efficiency of constructed phage-based biosorbent," Journal of Industrial Microbiology and Biotechnology, vol. 27, pp. 126-128 (2001); of record.*
Manafi et al., Microbiological Reviews, vol. 55, No. 3, pp. 335-348 (1991).*
Sun et al., Journal of Industrial Microbiology and Biotechnology, vol. 27, pp. 126-128 (2001).*
Manafi et al., Microbiological Reviews, vol. 55, No. 3, pp. 335-348 (1991) (of record).*
Sun et al., Journal of Industrial Microbiology and Biotechnology, vol. 27, pp. 126-128 (2001) (of record).*

(Continued)

*Primary Examiner* — Sharmila G Landau
*Assistant Examiner* — Paul D. Pyla
(74) *Attorney, Agent, or Firm* — Oliff PLC

(57) ABSTRACT

A method for detecting at least one microorganism that may be present in a sample, comprising the steps of:
 a) bringing into contact, in a container: a culture medium that enables the growth and/or detection of microorganisms, said sample and a sensitized solid support;
 b) subjecting the whole to a temperature that promotes the growth and/or detection of microorganisms; and
 c) observing, in real time, the appearance of an agglutination indicating the presence of the microorganism(s) or confirming said presence when said microorganisms are detected in said culture medium, when step b) has been completed, and a method for detecting and identifying at least one target microorganism that may be present in a sample.

29 Claims, 1 Drawing Sheet

(56) References Cited

OTHER PUBLICATIONS

Igarashi et al., Journal of Clinical Microbiology, vol. 23, No. 3, pp. 509-512 (1985).*
Fujikawa et al., Applied and Environmental Microbiology, vol. 54, No. 10, pp. 2345-2348 (1988).*
Scotland et al., Journal of Clinical Microbiology, vol. 27, No. 2, pp. 339-340 (1989).*
Feng, P., Molecular Biotechnology, vol. 7, pp. 267-278 (1997).*
Written Opinion of the International Searching Authority in International Application No. PCT/FR2009/050415; dated Sep. 17, 2009 (with English-language translation).
International Search Report in International Application No. PCT/FR2009/050415; dated Sep. 17, 2009 (with English-language translation).

\* cited by examiner

METHOD FOR THE REAL-TIME DETECTION OF MICROORGANISMS IN A LIQUID CULTURE MEDIUM BY AGGLUTINATION

The field of the invention is that of clinical or industrial microbiological testing. More particularly, it involves a method for identifying one or more microorganisms by means of an agglutination reaction carried out simultaneously with the enrichment of the sample in microorganisms.

Microbiological analysis requires precise techniques in which the time for obtaining the result should be as short as possible.

In the medical field, it is necessary to predict and diagnose the risk of infection: the faster and more precise the diagnosis, the more effective is the treatment of the patients and the more the risk of transmission is minimized. The approach is similar for animal health.

In the food-processing fields, the specifications are identical. These specifications distinguish, however, between pathogenic microorganisms and their toxins, the investigation of which applies to marketed products, nonpathogenic microorganisms, used as quality indicators for the production process, from the raw products to the final products, all along the chain, and bacteria of technological interest such as ferments. The rapid and precise detection of presumed contaminants makes it possible to test for them and to thus initiate corrective actions.

Technically, the microbiological analysis can implement one or more phases of pre-enrichment/enrichment, one or more phases of detection, one or more phases of counting of the microorganisms. For specific applications such as food-processing microbiological testing, a confirmation phase may also be required, in order to comply with the standards in force in this field.

The pre-enrichment/enrichment phase calls for selective or nonselective culture media well-known to those skilled in the art. Ready-to-use culture media, often in liquid form, based on formulations of conventional media are commercially available.

The detection phase is based on demonstrating the metabolic characteristics of the microorganisms being sought. Specific enzyme substrates are conventionally used. These enzyme substrates are generally composed of two parts, a first part specific for the enzyme activity to be revealed, also called target part, and a second part which acts as a label, also called label part, generally constituted of a chromophore or a fluorophore. Through the choice of these substrates, depending on whether or not there is a reaction, it is possible to characterize the nature of a microorganism or to distinguish various groups of microorganisms. Thus, the appearance or the disappearance of a coloration or of a fluorescence will be the signature of a microorganism genus or type. In this regard, the use of chromogenic media enables the simultaneous detection and identification of the microorganisms being sought. It simplifies the process and substantially reduces the time for obtaining the result. By way of concrete example, mention will be made of the applicant's ChromID® media. These chromogenic media are based on the detection of metabolic characteristics specific for the microorganisms being sought, for instance the beta-glucuronidase enzyme activity for *Escherichia coli*. However, some microorganisms, or some subtypes, for instance *Escherichia coli* O157 :H7, do not exhibit any specific enzyme activity and cannot therefore be detected using a chromogenic culture medium.

The confirmation phase, for its part, is more particularly linked to microbiological analysis in the food-processing field. Specifically, when the result of the previously developed methods is positive, it is necessary to confirm the presence of the pathogen being sought. This means that an additional test and the use of a principle of detection that is different than that used in the first analysis are required. Molecular biology techniques, based on the genomic characteristics of the microorganisms being sought, constitute one of the means used to confirm the identification. By way of example, mention will be made of conventional amplification techniques such as PCR (Polymerase Chain Reaction) and NASBA (Nucleic Acid Sequence Based Amplification), which can be coupled with real-time detection techniques known to those skilled in the art.

Immunoassays constitute another of the technologies used for the confirmation test. They make use of the immunogenic characteristics of the microorganisms being sought. Mention may be made, nonexhaustively, of the competition or sandwich ELISA (Enzyme Linked ImmunoSorbent Assay) techniques or the immunoagglutination techniques, detecting epitopes of the microorganisms being sought. The latter make use of functionalized solid supports, such as beads (for example, latex particles), coated with monoclonal or polyclonal antibodies, said functionalized supports being brought into contact with a biological sample, as indicated, for example, in the granted European patents EP 0 701 624 and EP 1 199 567. Alternatively, as described in patent U.S. Pat. No. 4,659,658, the solid particles can be coated with lectins which bind specifically to sugars located at the surface of a given microorganism. In any event, the appearance of the agglutination makes it possible to definitely identify the microorganism being sought.

The complete and precise identification of a microorganism in a sample therefore requires the sequence of several steps: enrichment, detection, confirmation. The standardization of routinely used tests has enabled the automation of the detection methods, which remain, however, slow to carry out. One drawback of the prior art is in fact that these steps are carried out sequentially. Another drawback is that the specific interaction reaction used for the confirmation step, which is an immunological reaction or a molecular hybridization reaction, is most commonly read at "end point". During this time, in the food-processing industry, the entire batch of final product is blocked while awaiting the result of the confirmation, and in clinical terms, the setting up of the relative antibiotic treatment and the preventive measures is delayed.

In view of the prior art considered, a method which combines the steps of enrichment, detection and precise identification is therefore lacking. Concretely, such a method would bring together rapidity, specificity and sensitivity.

The present invention therefore proposes to overcome the drawbacks described above by simultaneously using a culture of microorganisms and at least one agglutination reaction, in a liquid medium.

More specifically, the invention relates, firstly, to a method for detecting and identifying at least one microorganism that may be present in a sample, comprising the steps of:

a) bringing into contact, in a container: a culture medium that enables the growth and/or detection of microorganisms, said sample and a sensitized solid support;

b) subjecting the whole to a temperature that promotes the growth and/or detection of microorganisms;

c) observing, in real time, the appearance of an agglutination indicating the presence of the microorganism(s)

or confirming said presence when said microorganisms are detected in said culture medium, when step b) has been completed.

Another subject of the invention relates to a method for detecting and identifying at least one microorganism that may be present in a sample, comprising the steps of:
a) bringing into contact, in a container: a culture medium that enables the growth and/or identification of microorganisms, said sample and a sensitized solid support;
b) subjecting the whole to a temperature that promotes the growth and/or identification of microorganisms; and
c) observing, in real time, the appearance of an agglutination making it possible to identify the microorganism(s) or to confirm said identification, when said microorganism(s) is (are) identified in said culture medium, when step b) has been completed.

The invention relates, moreover, to a method for detecting and identifying at least one microorganism that may be present in a sample, comprising the steps of:
a) bringing into contact, in a container: a culture medium that enables the growth and identification of microorganisms, said sample and a sensitized solid support;
b) subjecting the whole to a temperature that promotes the growth and identification of microorganisms; and
d) observing, in real time, the appearance of an agglutination making it possible to supplement the identification of the microorganism(s), made when step b) has been completed.

The expression "supplement the identification" is intended to mean provide additional information making it possible to specify the identification of the microorganism. For example, in step a), the culture medium used may be specific for bacteria of the *Escherichia coli* genus and may comprise a substrate specific for this bacterial genus, such that the presence of such bacteria in the test sample is characterized by a modification of the culture medium, such as a change in color, if the substrate used is a chromogenic substrate. The agglutination observed in step c) may, for example, make it possible to demonstrate a particular strain of the *Escherichia coli* genus, such as *E. coli* O157:H7, which is an enteropathogenic strain.

The temperature that promotes the growth of microorganisms is between 20 and 44° C. and the sample is kept at this temperature for a period of time sufficient to enable the detection of microorganisms, i.e. a period of between 6 and 96 hours.

The combined use of these various techniques, in a single container, makes it possible both to save time and to limit handling, and therefore contamination of the handlers or of the samples, leading in the latter case to false-positives. In addition, the implementation of the invention can be automated. It would also be noted that the time saved is linked both to the combining of two steps into a single step and to the detection of the agglutination in real time and no longer at end point as in the confirmation techniques mentioned above.

Advantageously, steps a) and e) of the methods described above use chromogenic compounds (also called chromophores) or fluorescent compounds (also called fluorophores).

More particularly, the two methods of detection and identification can preferably use the appearance or disappearance of a coloration or of a fluorescence. Moreover, in all the methods which are subjects of the invention, the agglutination can advantageously be demonstrated by the appearance or the disappearance of a coloration or of a fluorescence.

Preferably, the container is taken from the group constituted of microplates, microcupules, microtubes, capillaries or multiwell cards.

Advantageously, the method which is the subject of the invention can also comprise a step of counting the microorganisms, preferably according to the most probable number method explained in patent EP 1 105 457 by the applicant.

According to one particular embodiment, the agglutination reaction carried out in step c) is an immunoagglutination reaction, demonstrating an antigen-antibody reaction.

According to another particular embodiment, the agglutination reaction carried out in step c) is a phage-bacterium reaction. More particularly, it is a reaction between a recombinant protein of a phage specific for a bacterial type and the corresponding bacterial molecule. Such interactions are described in patent EP 1 198 713.

According to another particular embodiment, the agglutination reaction carried out in step c) is a ligand/antiligand reaction.

According to another particular embodiment, the real-time detection of the agglutination reaction carried out in step c) according to one of the embodiments described above can make it possible to detect a sedimentation before appearance of the agglutination.

In addition, a subject of the invention is a diagnostic kit for carrying out the method according to the various embodiments developed above. The kit comprises:
  a container;
  a selective or nonselective culture medium, said culture medium optionally containing a substrate specific for the metabolism of the microbial genus or species to be detected; and
  a sensitized solid support.

Advantageously, the container is taken from the group constituted of microplates, microcupules, microtubes, capillaries or multiwell cards.

According to a first preferred embodiment, the sensitized support is a solid support-antigen complex or a solid support-antibody complex.

According to a second preferred embodiment, said sensitized support is a solid support-ligand complex or a solid support-antiligand complex. The ligand may comprise all or part of a bacteriophage.

The diagnostic kit according to the invention may also comprise at least one chromogenic or fluorescent compound.

Finally, a last subject of the invention relates to the use of a diagnostic kit according to the invention, for detecting and/or identifying at least one microorganism that may be present in a sample.

The invention will be understood more clearly on reading the detailed description and the nonlimiting examples which follow, in combination with the drawings in which.

Figure 1:
FIG. 1 represents a test strip for characterizing the bacterial origin of mammitis/mastitis, before incubation.

The method which is the subject of the invention can be used for samples of food, environmental or clinical origin. The sample is defined as a small part or small amount isolated from an entity for analysis.

Among the samples of food origin, mention may be made, nonexhaustively, of a sample of milk products (yogurts, cheeses, etc.), of meat, of fish, of eggs, of fruit, of vegetables, of water or of a drink (milk, fruit juice, soda, etc.). These samples of food origin may also come from prepared dishes or sauces. Finally, a food sample may be derived from an animal feed, such as, in particular, animal meals.

Mention will also be made of samples related to the environment, such as samples taken from a surface, from water or from the air.

The samples of clinical origin may correspond to biological fluid (whole blood, serum, plasma, urine, cerebrospinal fluid) samples taken, fecal samples taken, samples taken from the nose, the throat, the skin, wounds, organs, tissues or isolated cells, etc.

The microbiological testing corresponds to the analysis of a sample with the aim of isolating and/or identifying and/or counting the microorganisms potentially present, such as bacteria or yeast. Technically, this analysis comprises the growth, in vitro, of the microorganisms in a culture medium. The term "culture medium" is intended to mean a medium comprising all the components necessary for the survival and/or growth of microorganisms. The culture medium may contain optional additives such as, for example: peptones, one or more growth factors, carbohydrates, one or more selective agents, buffers, one or more gelling agents, etc. This culture medium may be in a liquid or gel form that is ready to use, i.e. ready for seeding in a tube or flask or on a Petri dish.

For the purpose of the present invention, the term "microorganism" covers Gram-positive or Gram-negative bacteria, yeasts and, more generally, unicellular organisms, invisible to the naked eye, which can be handled and multiplied in the laboratory.

In general, the culture medium may in addition contain a substrate for detecting an enzyme activity or a metabolic activity of the target microorganisms by means of a directly or indirectly detectable signal. For direct detection, this substrate can be linked to a part which acts as a label, which may be fluorescent or chromogenic. For indirect detection, the culture medium according to the invention may in addition comprise a pH indicator, sensitive to the variation in pH induced by the consumption of the substrate and revealing the growth of the target microorganisms. Said pH indicator may be a chromophore or a fluorophore. As examples of chromophores, mention will be made of neutral red, aniline blue and bromocresol blue. The fluorophores comprise, for example, 4-methylumbelliferone, aminocoumarin derivatives and resorufin derivatives.

For the purpose of the present invention, the identification of the microorganism being sought, potentially carried out by searching for its metabolic characteristics, should be confirmed. This confirmation can make use of agglutination reactions.

The term "agglutination" is intended to mean the result of an interaction between microorganisms and particles, said particles being either of natural origin, such as immunoglobulins M, or of solid support type, such as polymers. By means of this interaction, microorganisms and particles aggregate, adhere to one another and form a network. Said network is capable of sedimenting or of precipitating. The interaction between the microorganisms and the particles can lead to prior sedimentation, that the real-time observation will make it possible to detect before the complete formation of the network. The agglutination reactions comprise immunological reactions, such as antigen-antibody reactions, or more generally specific interactions between proteins. The network or complex formed by said specific reaction is then detected, either visually, or automatically by means of an optical system. Alternatively, the amount of complex formed can be determined.

Any one of the various methods known to those skilled in the art for carrying out an agglutination reaction can be used. The solid support is chosen from natural materials, synthetic materials which are optionally chemically modified, and in particular from latices, polymers of polyvinyl chloride), polyethylene, polystyrene or polyacrylate type, and copolymers of the type of those based on styrene. Such a solid support may be in the form of particles.

The term "sensitized support" is intended to mean the binding, to said solid support, of functional compounds comprising antigens, antibodies, whole phages or phage proteins.

The term "antigen" denotes a compound capable of being recognized by an antibody of which it has induced the synthesis via an immune response.

The term "antibody" includes polyclonal or monoclonal antibodies, antibodies obtained by genetic recombination and antibody fragments.

Phages, or bacteriophages, are viruses that infect only bacteria; they are also called bacterial viruses. In the agglutination reactions, they are used for their proteins which recognize a given bacterial strain or species with great specificity and great sensitivity.

The binding to a solid support can correspond to a direct or indirect immobilization: the term "direct immobilization" is intended to mean binding by covalence or passive adsorption; a direct immobilization can be carried out by means of a ligand chemically bound to said solid support. The term "indirect immobilization" is intended to mean the ligand/antiligand interaction between a ligand bound to the antigen, the antibody or the phage (more broadly, the functional compound) and the antiligand or complementary ligand bound to the solid support.

The ligand/antiligand pairs are well known to those skilled in the art, and mention may, for example, be made of the following pairs: biotin/streptavidin, hapten/antibody, antigen/antibody, peptide/antibody, sugar/lectin, polynucleotide/polynucleotide complementary thereto. A water-soluble derivative of a maleic anhydride homopolymer or copolymer, such as those developed by the applicant in the granted patent EP 0 561 722, may also be used to immobilize a biological molecule. These solid supports can be distributed in the reaction in various forms: freeze-dried, in liquid suspension, in the form of beads such as those commercially available under the trade mark BioBall®, etc. The agglutination can be detected visually, or by means of an automatic optical reader according to various principles known to those skilled in the art, among which mention will be made, nonexhaustively, of:

(1) the detection of the appearance of a fluorescence, through the sedimentation of a colored latex which absorbs the fluorescence initially present in the medium;

(2) the detection of a change in color through the mixing of the colored latex particles with the potentially colored matrix;

(3) the concentration of fluorescence through the agglutination of the fluorescent latex particles, leading to a disappearance of the diffuse fluorescence in the medium;

(4) the disappearance of color through the sedimentation of a colored latex present in the medium.

The fluorophores that can be used were mentioned above and comprise 4-methylumbelliferone, aminocoumarin derivatives or resorufin derivatives.

The operations of culturing/identification and then agglutination at end point, described in two steps, are, according to the present invention, combined in a single step, the specific agglutination being detected in real time. By way of illustration, mention will be made of the possible identification, in a sample of food origin, of *Listeria monocytogenes*, serotype 4b: the detection of *Listeria monocytogenes* can be carried out using a culture medium containing one or more substrates specific for the metabolism of this bacterium, and the identification of the serotype 4b will be carried out simultaneously by means of the agglutination reaction, detected in real time.

In one particular embodiment, the invention can be carried out in containers such as microplates, microcupules, microtubes, capillaries, etc.

Advantageously, the method according to the invention can be combined with an automatic microbiological testing device of TEMPO® type, as developed by the applicant, and can optionally enable counting of the detected microorganisms.

The method, which is the subject of the invention, can be carried out using a kit comprising: a reaction medium containing a nutritive base, sensitized particles and, optionally, a chromogenic substrate specific for the microorganism(s) being sought. Said medium is resuspended with an aliquot of the sample to be analyzed. Advantageously, the kit for carrying out the method according to the invention can also contain a solid container of microplate, microtube, microcupule, capillary, VITEK® card or TEMPO® card type.

EXAMPLES

Example 1

Double Counting of *Escherichia Coli* spp and *Escherichia Coli* O157 by Combining Phenotypic and Immunological Reactions The objective of this analysis is to simultaneously count *E. coli* spp enzymatically and *E. coli* O157 immunologically using the TEMPO® system marketed by the applicant.
Procedure:
Step 1: Resuspension of the Reaction Medium with an Aliquot of the Sample to be Analyzed:
The Reaction Medium Contains:
  an enzyme substrate specific for the *E. coli* species: 4-methylumbelliferyl-β-D-glucuronide (Biosynth ref. M-5700): nonfluorescent at T0 at 50 mg/l (can vary between 0.1 mg/l and 1000 mg/l);
  latex particles (Oxoïd, ref. DR0620M), blue-colored, sensitized with antibodies specific for *E. coli* O157, at 1% of dry extract (can vary between 0.1% and 10%);
  a nutritive base: peptones at the concentration of 10 g/l;
  an inhibitor system: bile salts at the concentration of 1.5 g/l.

The reaction medium resuspended in the sample (e.g. 4 ml of mains supply water) is then incorporated into a TEMPO® card with a view to performing a count.

Before incubation of the card, the wells of the latter are blue and nonfluorescent.
Step 2: Incubation of the Card:
The TEMPO® cards are then incubated at 37° C. for 24 h. During this incubation period, the reaction of agglutination of the particles sensitized with anti-*E. coli* O157 antibodies and the enzyme reaction (degradation of the *E. coli*-specific substrate) take place simultaneously with the bacterial growth, in the event of the target bacteria being present in the wells of the TEMPO® card.
Step 3: Reading of the Test After 24 h of Incubation:
Reaction positive for *E. coli* O157: there is formation of the anti-*E. coli* O157 antibody/*E. coli* O157 cell complex, resulting in agglutination of the latex particles and, consequently, disappearance of the blue coloration, subsequent to the formation of a blue precipitate at the bottom of the wells concerned.

Reaction positive for *E. coli* spp: appearance of fluorescence (release of fluorescent 4-methylumbelliferone molecules) in the positive well(s) after degradation of the substrate by *E. coli* spp.
Wells positive for *E. coli* spp and negative for *E. coli* O157: fluorescent and blue.
Wells positive for *E. coli* spp and *E. coli* O157: fluorescent and uncolored (+blue precipitate at the bottom of the well).
Wells negative for *E. coli* spp and *E. coli* O157: nonfluorescent and blue.

The *E. coli* O157- and *E. coli* spp-positive wells are then counted in order to determine, via the MPN table (internal algorithm), the number of colony forming units (CFU) of *E. coli* O157 and *E. coli* spp per gram of sample.

Example 2

Characterization of the Bacterial Origin of a Case of Mammitis/Mastitis in Dairy Cows/Sheep/Goats with a View to Adopting an Appropriate and Effective Antibiotic Treatment Mammitis results from an infection of the udder by bacteria more or less suited to this biotope. Several bacteria are responsible for this type of infection, and are classified in two groups: mammary reservoir bacteria (e.g. *Staphylococcus aureus, Streptococcus* spp) and environmental bacteria (e.g. *Escherichia coli, Klebsiella* spp).

Principle of the test: characterization of the bacterial origin of a case of mammitis by agglutination of sensitized particles, in suspension in a liquid medium, with the target bacterial cells (i.e. *Staphylococcus aureus, Streptococcus* spp, *Escherichia coli, Klebsiella* spp).
Procedure:
Step 1: Resuspension of the Reaction Medium with an Aliquot of the Sample to be Analyzed (e.g. Milk):
The test is in the form of a strip comprising 4 wells containing the reaction medium. The composition of the reaction medium is the following:
blue particles sensitized with phage proteins and/or antibodies (Ab) specific for the targets: *Staphylococcus aureus* (well No. 1), *Streptococcus* spp (well No. 2), *Escherichia coli* (well No. 3), *Klebsiella* spp (well No. 4);
a nutritive base: buffered peptone water (Ref bMx 51094).
Each well is resuspended with 500 µl of sample.
Initial state of the strip before incubation (absence of reaction): all the wells of the strip are blue, given the absence of agglutination and of sedimentation at T0 of the anti-target sensitized blue particles (cf. FIG. 1).
Step 2: Incubation of the Strip:
The strip is then incubated at 37° C. for 4 to 16 h. During this incubation period, the reaction of agglutination of the anti-target sensitized particles takes place simultaneously with the bacterial growth, in the event of contamination of the well by the target bacterium responsible for the mammitis investigated.

Figure 2:
FIG. 2 represents the test strip after incubation, with a reaction positive for *Staphylococcus aureus*.
Figure 3:
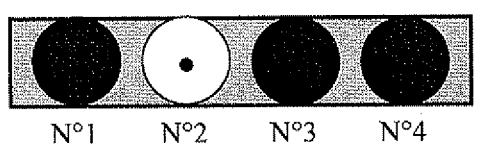
FIG. 3 represents the test strip after incubation, with a reaction positive for *Streptococcus* spp.
Figure 4:
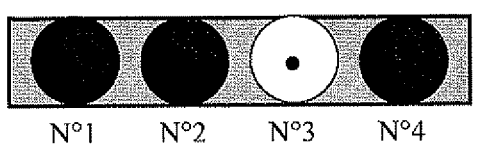
FIG. 4 represents the test strip after incubation, with a reaction positive for *Escherichia coli*.
Figure 5:
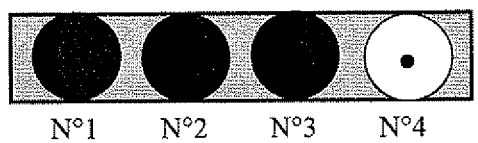
FIG. 5 represents the test strip after incubation, with a reaction positive for *Klebsiella* spp.

Step 3: Reading of the Test After 4 to 16 h of Incubation:
Positive reaction: formation of the phage protein/bacterium or antibody/bacterial antigen complex resulting in agglutination of the latex particles (formation of a precipitate at the bottom of the well) and, consequently, disappearance of the blue coloration in the wells concerned. Various cases can be envisioned:
In the case where the mammitis is due to *Staphylococcus aureus*, disappearance of the blue coloration occurs in well No. 1 (cf. FIG. 2).
In the ease where the mammitis is due to *Streptococcus* spp, disappearance of the blue coloration occurs in well No. 2 (cf. FIG. 3).
In the case where the mammitis is due to *Escherichia coli*, disappearance of the blue coloration occurs in well No. 3 (cf. FIG. 4).
In the case where the mammitis is due to *Klebsiella* spp, disappearance of the blue coloration occurs in well No. 4 (cf. FIG. 5).

Example 3

Counting *Salmonella* on the TEMPO® Platform

The objective of this analysis is to count *Salmonella* immunologically by agglutination of particles sensitized with recombinant phage proteins, using the TEMPO® system marketed by the applicant.
Procedure:
Step 1: Adsorption of the Anti-*Salmonella* B D1 Phage Proteins
This step consists in adsorbing the phage proteins at the surface of particles:
reference: anti-B-D1 phage proteins 2.67 mg/ml,
latex used, supplied by Polymer Laboratories: Plain fluorescent yellow PL FY batch CD 222: 311 nm
The phage proteins are adsorbed at the concentration of 140 μg/ml in 20 mM phosphate buffer, pH 7.2. The test volume is 200 μl. The latex particles are introduced into the medium in a proportion of 5 mg/ml.
The adsorption is carried out with agitation on a revolving wheel for 15 hours.
Testing of the Adsorption Yield:
centrifugation of 50 μl of the sample and recovery of the supernatant;
assaying of the supernatant by the BCA protein assay method;
yield calculated relative to the standard curve and relative to the initial concentration of the phage protein used for the test.
This yield is 73%.
The size of the particles is measured on a particle sizer.
It is 311 nm for the PL FY latex and 315 nm for the particle-phage protein conjugates.
Step 2: Incubation in the TEMPO® Card:
The Reaction Medium Contains:
3.5 ml of nutritive base: peptones at the concentration of 10 g/l;
a sample containing 50 CPU of bacteria *Salmonella bareilly* 06.03.927 IM1272: $C_1$;
0.5 ml of fluorescent latex particles sensitized with *Salmonella*-specific phage proteins at 0.5% of dry extract.
The reaction medium is then incorporated into a TEMPO® card with a view to performing a count.
Before incubation of the card, the wells of the latter are fluorescent.

The TEMPO® cards are then incubated at 37° C. for 24 h. During this incubation period, the reaction of agglutination of the particles sensitized with the anti-B-D1 phage proteins takes place simultaneously with the bacterial growth, in the event of the target bacteria being present in the wells of the TEMPO® card.
Step 3: Reading of the Test After 24 h of Incubation:
Reaction positive for *Salmonella bareilly*: there is formation of the phage protein/*Salmonella bareilly* cell complex, resulting in agglutination and sedimentation of the latex particles. Consequently, a concentration of the fluorescence at the bottom of the wells concerned and a disappearance of the fluorescence in the reading window are observed.
Negative reaction: the fluorescence remains homogeneous throughout the well.
The positive wells are then counted so as to determine, via the MPN table (internal algorithm), the number of colony forming units (CFU) of *Salmonella bareilly* 06.03.927 IM1272: $C_1$ per gram of sample.
The result of the count is 11 CFU/ml, i.e. 44 CFU introduced, in accordance with the theoretical 50 CFU.

The invention claimed is:

1. A method for detecting whether at least one microorganism is present in a sample, comprising:
subjecting a mixture including the sample, a sensitized solid support, and a culture medium in a container to culturing conditions for 4 to 96 hours so as to culture the microorganism when present in the sample such that the microorganism is multiplied; and
measuring in real time an amount of binding of the microorganism to the sensitized solid support at a plurality of time points during the 4 to 96 hours of culturing;
wherein:
the microorganism is a unicellular organism;
the sensitized solid support includes (i) a solid support, and (ii) an antigen, antibody, phage, phage protein, antiligand, or ligand that enables binding between the microorganism and the sensitized solid support;
binding of the microorganism to the sensitized solid support indicates that the microorganism is present in the sample; and
the binding of the microorganism to the sensitized solid support takes place simultaneously with the multiplication of the microorganism when present in the sample.

2. The method of claim 1, further comprising measuring a number of colony forming units (CFU) of the microorganism when the microorganism is present in the sample.

3. The method of claim 2, wherein the number of CFU is measured according to the most probable number method.

4. The method of claim 2, wherein the number of CFU is measured using an automatic microbiological testing device.

5. The method of claim 1, wherein the sample is a food sample.

6. The method of claim 1, wherein the microorganism comprises a species of *Listeria, Staphylococcus, Streptococcus, Escherichia, Klebsiella,* or *Salmonella*.

7. The method of claim 1, wherein the microorganism is *Listeria monocytogenes*.

8. The method of claim 1, wherein the culture medium is a selective medium.

9. The method according to claim 1, further comprising detecting whether there is a change in the culture medium in the same container independent of the binding of the microorganism to the sensitized solid support, wherein detection of the change in the culture medium indicates that the microorganism was present in the sample and measuring the amount of binding confirms that the microorganism was present in the sample.

10. The method of claim 9, wherein the change in the culture medium is detected by the appearance or the disappearance of a coloration or fluorescence.

11. The method of claim 1, further comprising detecting a chromogenic or fluorescent detectable signal in the culture medium, wherein the culture medium includes a chromogenic or fluorescent enzymatic substrate that directly detects an enzymatic activity of the microorganism when present in the sample, and the microorganism causes the enzymatic substrate to produce the chromogenic or fluorescent detectable signal, which is independent of the binding of the microorganism to the sensitized solid support.

12. The method of claim 1, wherein the container is selected from the group consisting of microplates, microcupules, microtubes, capillaries, and multiwall cards.

13. The method of claim 1, wherein binding of the microorganism to the sensitized solid support results from an antigen-antibody reaction, a phage-bacterial protein reaction, or a ligand-antiligand reaction between the cultured microorganism and the sensitized solid support.

14. The method according to claim 1, wherein the amount of binding of the microorganism to the sensitized solid support is automatically measured by an automated optical reader.

15. The method according to claim 1, further comprising identifying the at least one microorganism, wherein binding of the microorganism to the sensitized solid support indicates a positive identification of the microorganism.

16. The method according to claim 1, wherein the microorganism is a bacterium, the culture medium is specific for a genus of the bacterium, and the sensitized solid support for is specific for a strain of the bacterium.

17. The method according to claim 1, wherein the amount of binding of the microorganism to the sensitized solid support is measured at a plurality of time points between 4 to 16 hours after culturing begins.

18. The method according to claim 1, wherein the amount of binding of the microorganism to the sensitized solid support is measured at a plurality of time points at least 24 hours after culturing begins.

19. A method for detecting whether at least one microorganism is present in a sample, comprising:
subjecting a mixture including the sample, a sensitized solid support, and a culture medium in a container to culturing conditions for 4 to 96 hours so as to culture the microorganism when present in the sample such that the microorganism is multiplied; and
periodically measuring in real time an amount of binding of the microorganism to the sensitized solid support during culturing;
wherein:
the microorganism is a unicellular organism;
the sensitized solid support includes (i) a solid support, and (ii) an antigen, antibody, phage, phage protein, antiligand, or ligand that enables direct binding between the microorganism and the sensitized solid support;
binding of the microorganism to the sensitized solid support indicates that the microorganism is present in the sample; and
the binding of the microorganism to the sensitized solid support takes place simultaneously with the multiplication of the microorganism when present in the sample.

20. The method of claim 19, further comprising measuring a number of colony forming units (CFU) of the microorganism when the microorganism is present in the sample.

21. The method of claim 19, wherein the sample is a food sample.

22. The method of claim 19, wherein the microorganism is *Listeria monocytogenes*.

23. The method according to claim 19, wherein the amount of binding of the microorganism to the sensitized solid support is measured at a plurality of time points at least 24 hours after culturing begins.

24. A method for detecting whether at least one microorganism is present in a sample, comprising:
subjecting a mixture including the sample, a sensitized solid support, and a culture medium in a container to culturing conditions for 4 to 96 hours so as to culture the microorganism when present in the sample such that the microorganism is multiplied; and
periodically measuring in real time an amount of binding of the microorganism to the sensitized solid support during culturing;
wherein:
the microorganism comprises a species of *Listeria*;
the sensitized solid support includes (i) a solid support, and (ii) an antibody that enables direct binding between the microorganism and the sensitized solid support;
binding of the microorganism to the sensitized solid support indicates that the microorganism is present in the sample; and
the binding of the microorganism to the sensitized solid support takes place simultaneously with the multiplication of the microorganism when present in the sample.

25. The method of claim 24, wherein the microorganism is *Listeria monocytogenes*.

26. The method of claim 24, further comprising measuring a number of colony forming units (CFU) of the microorganism when the microorganism is present in the sample.

27. The method of claim 24, wherein the sample is a food sample.

28. The method of claim 24, wherein the amount of binding of the microorganism to the sensitized solid support is measured at one or more time points at least 24 hours after culturing begins.

29. The method of claim 1, wherein the microorganism is selected from the group consisting of *Escherichia coli, Listeria monocytogenes, Staphylococcus aureus, Streptococcus* spp, *Klebsiella* spp, and *Salmonella bareilly*.

* * * * *